United States Patent
Rafailovich et al.

(10) Patent No.: US 8,367,117 B2
(45) Date of Patent: Feb. 5, 2013

(54) NANOCOMPOSITE HYALURONIC ACID-CLAY BASED HYDROGELS

(75) Inventors: Miriam Rafailovich, Plainview, NY (US); Divya Bhatnagar, Stony Brook, NY (US); Mary K. Cowman, Mohegan Lake, NY (US)

(73) Assignees: The Research Foundation of State University of New York, Albany, NY (US); Polytechnic Institute of New York University, Brooklyn, NY (US)

( * ) Notice: Subject to any disclaimer, the term of this patent is extended or adjusted under 35 U.S.C. 154(b) by 20 days.

(21) Appl. No.: 13/104,605

(22) Filed: May 10, 2011

(65) Prior Publication Data

US 2011/0275572 A1    Nov. 10, 2011

Related U.S. Application Data

(60) Provisional application No. 61/332,976, filed on May 10, 2010.

(51) Int. Cl.
*A61K 9/14* (2006.01)

(52) U.S. Cl. ...................................................... 424/489

(58) Field of Classification Search .................. None
See application file for complete search history.

(56) References Cited

U.S. PATENT DOCUMENTS 4,920,158 A * 4/1990 Murray et al. ............... 523/111
2010/0266512 A1 10/2010 Wenk et al.

* cited by examiner

*Primary Examiner* — Susan Tran
(74) *Attorney, Agent, or Firm* — Hoffmann & Baron, LLP

(57) ABSTRACT

Hydrogels formed from hyaluronic acid, a nanoclay and gelatin-type A. The hyaluronic acid is preferably dissolved in a cell culture medium containing amino acids, salts, glucose, vitamins and an antibiotic to form a hyaluronic acid solution. The gelatin-type A has a weight/volume of from about 0.02% to 0.08%. The nanoclay is exfoliated in deionized water and preferably includes $SiO_2$, $MgO$, $Na_2O$ and $Li_2O$.

8 Claims, No Drawings

NANOCOMPOSITE HYALURONIC ACID-CLAY BASED HYDROGELS

This application claims priority based on provisional application Ser. No. 61/332,976, filed on May 10, 2010, which is incorporated herein by reference in its entirety.

This invention was made with government support under grant number DMR 0606387 awarded by the National Science Foundation, Division of Materials Research. The government has certain rights in the invention.

FIELD OF THE INVENTION

The present invention relates to hyaluronic acid ("HA") hydrogels. In particular, the present invention relates to HA hydrogels combined with nanocomposite clays.

BACKGROUND OF INVENTION

Tissue engineering uses a combination of cells, engineering materials and suitable biochemical and physio-chemical factors to improve or replace biological functions. One approach to tissue engineering is to create an environment using cells within an artificially-created support system that attempts to mimic the environment of tissue development in vivo (i.e., like the conditions in the body). Two important components of creating tissue are a scaffold and a bioreactor. A scaffold is a three dimensional ("3D") structure optimized for cell attachment and tissue growth. The scaffold is inserted into a bioreactor, which is the culture vessel that provides conditions that are dynamic and similar to in vivo conditions.

To achieve the goal of tissue reconstruction, scaffolds must meet specific requirements. A high porosity and an adequate pore size are necessary to facilitate cell seeding and diffusion throughout the whole structure of both cells and nutrients. Biodegradability is often an essential factor since scaffolds should preferably be absorbed by the surrounding tissues without the necessity of a surgical removal. The scaffold is designed so that the rate at which degradation occurs closely coincides with the rate of tissue formation. While the cells are fabricating their own natural matrix structure around themselves, the scaffold provides structural integrity within the body. When the scaffold degrades, the newly formed tissue takes over the mechanical load. For clinical uses, it is desirable for the scaffold material to be injectable.

Cells are often implanted or "seeded" into the scaffolds, which can serve one or more functions: (1) allow cell attachment and migration; (2) deliver and retain cells and biochemical factors; (3) enable diffusion of vital cell nutrients and expressed products; and (4) exert certain mechanical and biological influences to modify the behavior of the cell phase. In general, bioreactors are used to: (1) establish uniform cell distribution on the scaffold; (2) maintain desired amounts of nutrients and gases; and (3) expose developing tissue to physical stimuli, which modifies tissue development.

Many different materials (natural and synthetic, biodegradable and permanent) have been investigated for use as scaffold materials. Most of these materials have been known in the medical field for uses other than tissue engineering, such as bioresorbable sutures. Examples of these materials are collagen and some polyesters. Scaffolds may also be constructed from natural materials. In particular, different derivatives of the extracellular matrix have been studied to evaluate their ability to support cell growth. Proteic materials, such as collagen or fibrin, and polysaccharidic materials, like chitosan or glycosaminoglycans (GAGs), have all proved suitable in terms of cell compatibility, but some issues with potential immunogenicity still remains. Among GAGs hyaluronic acid, possibly in combination with cross linking agents (e.g. glutaraldehyde, water soluble carbodiimide, etc.), is one of the possible choices as scaffold material.

Hyaluronic acid (HA) (also called hyaluronic acid or hyaluronate) is a naturally occurring polymer found in every tissue of the body. It is particularly concentrated in the skin (almost 50% of the HA in the body is found in the skin) and synovial fluid. HA is an anionic, nonsulfated glycosaminoglycan consisting of repeating disaccharides of alternating D-glucuronic acid and N-acetylglucosamine molecules. It is a straight-chained polymer with a molecular weight that varies between 50,000 and 13,000,000 daltons. Hyaluronic acid is naturally present in the pericellular gels, in the fundamental substance of connective tissue and in vertebrate organisms, of which it is one of the chief components, in the synovial fluid of joints, in the vitreous humor, in the human umbilical cord tissues and in rooster combs. One of the chief components of the extracellular matrix, hyaluronan contributes significantly to cell proliferation and migration, and may also be involved in the progression of some malignant tumors.

Hyaluronic acid plays a vital role in many biological processes. For example, hyaluronic acid is applied in the tissue repair process, especially in the early stages of granulation, stabilizing the coagulation matrix and controlling its degradation. When skin is exposed to excessive UVB rays, it becomes inflamed (sunburn) and the cells in the dermis stop producing as much hyaluronan, and increase the rate of its degradation. Hyaluronan degradation products also accumulate in the skin after UV exposure. The application of hyaluronic acid solutions has been found to accelerate healing in patients suffering from sores, wounds and burns. It is also known that hyaluronic acid fractions can be used to facilitate tissue repair, as substitutes for the intraocular fluid, or they can be administered by the intra-articular route to treat joint pathologies.

The physiological activity of HA polymers and oligomers makes it a promising material for a variety of applications. HA gels are popular for cell culture scaffolds in tissue engineering. However, HA must be crosslinked to achieve the proper mechanical properties and not be digested by HA aces enzymes (i.e., angiotensin-converting enzyme). Most commercially available HA hydrogels are chemically crosslinked where the chemicals are cytotoxic. In addition, these chemicals are expensive and drive up the prices of the gels so they are not commercially viable.

Accordingly, there is a need for less expensive HA-hydrogel scaffolds that are non-toxic and have biochemical functionality and improved mechanical stability against degradation.

SUMMARY OF THE INVENTION

In accordance with the present invention, HA clay based hydrogels are provided. In their simplest form, the hydrogel includes hyaluronic acid ("HA") and a nanoclay. The nanoclay preferably includes about 55-65% $SiO_2$, 20-35% MgO, 1-5%, $Na_2O$ and 0.2-2% $Li_2O$. The HA has a weight/volume of 0.02% to 0.08% and is preferably dissolved in a cell culture medium containing amino acids, salts, glucose, vitamins and an antibiotic to form a HA solution. The HA solution can also include an antibiotic. The HA solution to nanoclay ratio is from about 1:3 to about 1:25 and preferably from about 1:5 to 1:20.

In another embodiment, the hydrogel includes hyaluronic acid ("HA"), a nanoclay and gelatin-type A. The HA is preferably dissolved in a cell culture medium containing amino acids, salts, glucose, vitamins and an antibiotic to form a HA solution and the nanoclay is exfoliated in deionized water. The gelatin-type A has a weight/volume of from about 0.02% to 0.08% and the volume ratio of HA solution to gelatin-type A is from about 8:5 to about 5:8 and preferably about 1:1. The nanoclay preferably includes about 55-65% $SiO_2$, 20-35% MgO, 1-5%, $Na_2O$ and 0.2-2% $Li_2O$ and has a weight/volume of from about 0.01% to about 0.08%. The HA solution to nanoclay ratio is from about 1:3 to about 1:25 and preferably from about 1:5 to 1:20. The volume ratio of HA/gelatin-type A mixture to clay is from about 1:5 to about 1:20.

The hydrogel can include 5-30 percent by weight HA, 5-30 percent by weight gelatin and preferably 10-25 percent by weight HA, 10-25 percent by weight gelatin. The hydrogel can also include 5-30 percent by weight HA, 5-30 percent by weight gelatin and 40-90 percent by weight nanoclay and preferably 10-25 percent by weight HA, 10-25 percent by weight gelatin and 50-80 percent by weight nanoclay.

DETAILED DESCRIPTION OF THE INVENTION

In accordance with the present invention, HA clay based hydrogels are provided. The present invention uses a safer method to construct the HA scaffolds without the use of any toxic chemical additives. Instead, synthetic layered silicate clays with low heavy metals content are used to achieve the same goals of crosslinking. The clay crosslinking agents are preferably nanoclays, most preferably hectorite, a trioctohedral clay mineral of the montmorillonite group composed of a hydrous silicate of magnesium and lithium. The inexpensive and non toxic clays are rheology modifiers that increase cell strength and promote cell adhesion. In water or aqueous solutions of alcohols, the clays form highly thixotropic clear and colorless gels. A preferred clay is Laponite® XLG clay sold by Southern Clay Products, Inc. of Gonzales, Tex.

The hyaluronic acid (HA) hydrogels are made from non-functionalized HA obtained by crosslinking with a nanoclay (i.e., nanoparticles of layered mineral silicates). The entangled polymer chains of HA are adsorbed on the clay platelets resulting in stable homogeneous hydrogels. Clay cannot be exfoliated or dissolved in any salt solutions whereas these hydrogels remain stable in buffer solutions. The clay is exfoliated in deionized water and then dissolved in a medium for maintaining cells in tissue culture, i.e., "a cell culture medium," that includes amino acids, salts, glucose, vitamins, and optionally iron and phenol red. A preferred medium is serum free Dulbecco's modified Eagle's medium ("DMEM"), i.e., DMEM supplemented by an antibiotic, such as 1% Pen-Strep. The HA solution and the exfoliated clay solution are mixed in different volume ratios, while maintaining a temperature of between about 35 to 40° C., preferably a temperature of about 37° C., to obtain a gel. The HA solution to clay ratio is preferably from about 1:3 to about 1:25, more preferably from about 1:5 to about 1:20 and most preferably from about 1:10 to 1:15.

The HA hydrogels are combined with clay crosslinking agents to form rigid hydrogels, which are non-toxic, inexpensive and cell friendly. These rigid hydrogels have an elastic modulus equivalent to commercially available HA-PEGDA (polyethylene glycol diacrylate) hydrogels and are non-toxic. The clays can be modified hectorite clays that contain lithium, sodium, magnesium and silicate. Preferably, these modified hectorite clay compositions contain about 55-65% $SiO_2$, 20-35% MgO, 1-5%, $Na_2O$ and 0.2-2% $Li_2O$. The most preferred clays contain about 59.5% $SiO_2$, 27.5% MgO, 2.8%, $Na_2O$ and 0.8% $Li_2O$.

In a preferred embodiment, the clay is a synthetic, layered, colloidal silicate with low heavy metal content that is insoluble in water but hydrates and swells to give clear and colorless colloidal dispersions in water or aqueous solutions of alcohols. At concentrations of 2% or greater in water, highly thixotropic, heat stable gels are obtained, which impart viscosity and suspension properties to various types of formulations.

The HA-clay based hydrogels of the present invention are biodegradable, viscoelastic with varying moduli and can support cell adhesion. The HA hydrogels in the prior art do not promote cell adhesion and require fibronectin coating cell attachment for cell adhesion. In contrast, the HA-clay based hydrogels of the present invention, when coated with gelatin, do not require fibronectin in order for cells to attach and proliferate.

The HA-clay based hydrogels avoid the need for fibronectin by mixing HA and gelatin Type A (a gelatin derived from an acid-treated precursor) before mixing with clay in different volume ratios to obtain a rigid hydrogel. Gelatin is derived from collagen, an insoluble fibrous protein that occurs in vertebrates and is the principal constituent of connective tissues and bones. Collagen is distinctive in that it contains an unusual high level of the cyclic amino acids proline and hydroxyproline. Collagen consists of three helical polypeptide chains wound around each other and connected by inter-molecular cross-links. Gelatin is recovered from collagen by hydrolysis. There are several varieties of gelatin, the composition of which depends on the source of collagen and the hydrolytic treatment used. A preferred gelatin-type A is derived from porcine skin.

The hydrogels are made by dissolving HA having about a 0.02% to 0.08% weight/volume ("(w/v)") in a cell culture medium to form a HA solution. The HA solution is then mixed with gelatin-type A having about a 0.02% to 0.08% (w/v) in a volume ratio of from about 8:5 to about 5:8 and preferably from about 6:5 to about 5:6. Most preferably, about 0.5% (w/v) HA and about 0.5% (w/v) gelatin-type A are mixed in a volume ratio of about 1:1. The HA/gelatin-type A mixture is then mixed with clay having about a 0.01% to 0.08% (w/v) in different volume ratios. The preferred volume ratio of HA/gelatin-type A mixture to clay is from about 1:5 to about 1:20 and the most preferred volume ratio is from about 1:10 to about 1:15. Different mixing volume ratios give different stiffness of the hydrogels which is a very important factor for migration of cells in wound healing applications.

Unlike currently available HA constructs, the HA-clay based hydrogels do not require fibronectin and are non-toxic. A coating of gelatin on these HA hydrogels can promote cell adhesion and proliferate well over a period of 2 weeks.

EXAMPLES

The examples set forth below serve to provide further appreciation of the invention but are not meant in any way to restrict the scope of the invention.

Example 1

HA-clay based hydrogels of the present invention were made from non-functionalized HA by crosslinking with Laponite XLG clay manufactured by Rockwood Additives Ltd., Cheshire, United Kingdom. 3% (w/v) clay was exfoliated in deionized water and 0.5% (w/v) HA was dissolved in serum free DMEM (Dulbecco/Vogt modified Eagle's minimal essential medium), i.e., DMEM supplemented by 1%

Pen-Strep. The HA and clay solutions were mixed in different volume ratios to obtain gels with varying rigidity when kept at 37 degrees Celsius.

Example 2

HA-clay based hydrogels of the present invention were made by mixing 0.5% (w/v) HA and 0.5% (w/v) gelatin-type A (porcine skin) in 1:1 volume ratio to form a first solution. A second solution was formed by exfoliating 3% (w/v) clay in deionized water. The HA/gelatin solution was then mixed with the clay solution in different volume ratios to obtain rigid hydrogels.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

We claim:

1. A hydrogel comprising:
    hyaluronic acid ("HA");
    a nanoclay; and
    gelatin-type A
    wherein the HA is dissolved in a cell culture medium containing amino acids, salts, glucose, vitamins and an antibiotic to form a HA solution;
    wherein the hydrogel comprises 5-30 percent by weight HA, 5-30 percent by weight gelatin-type A, and about 40-90 percent by weight nanoclay; and
    wherein the nonclay comprised about 55-65% $SiO_2$, 20-35% MgO, 1-5%, $Na_2O$ and 0.2-2% $LiO_2O$.

2. The hydrogel according to claim 1, wherein the nanoclay is exfoliated in deionized water.

3. The hydrogel according to claim 1, wherein the gelatin-type A has a weight/volume of from about 0.02% to 0.08%.

4. The hydrogel according to claim 3, wherein the HA solution and gelatin-type A have a volume ratio of from about 8:5 to about 5:8.

5. The hydrogel according to claim 3, wherein the HA solution and gelatin-type A have a volume ratio of about 1:1.

6. The hydrogel according to claim 3, wherein the nanoclay has a weight/volume of from about 0.01% to about 0.08%.

7. The hydrogel according to claim 3, wherein the volume ratio of HA/gelatin-type A mixture to clay is from about 1:5 to about 1:20.

8. The hydrogel according to claim 3, wherein the hydrogel comprises 10-25 percent by weight HA, 10-25 percent by weight gelatin and about 50-80 percent by weight nanoclay.

* * * * *

UNITED STATES PATENT AND TRADEMARK OFFICE
CERTIFICATE OF CORRECTION

PATENT NO.         : 8,367,117 B2
APPLICATION NO.    : 13/104605
DATED              : February 5, 2013
INVENTOR(S)        : Rafailovich et al.

It is certified that error appears in the above-identified patent and that said Letters Patent is hereby corrected as shown below:

IN THE SPECIFICATION:

Column 2, line 32:

Now reads:    "and bums."

Should read:    -- and burns. --

Column 2, lines 63-64:

Now reads:    "from about a 1:3 to about 1:25 and preferably from about 1:5 to 1:20."

Should read:    -- from about a 6:1 to about 1:2 and preferably from about 3:1 to 1:1. --

Column 3, lines 9-10:

Now reads:    "from about a 1:3 to about 1:25 and preferably from about 1:5 to 1:20."

Should read:    -- from about a 6:1 to about 1:2 and preferably from about 3:1 to 1:1. --

Column 3, line 11:

Now reads:    "from about 1:5 to about 1:20."

Should read:    -- from about 5:1 to about 1:2. --

Signed and Sealed this
Twenty-first Day of May, 2013

Teresa Stanek Rea
*Acting Director of the United States Patent and Trademark Office*

CERTIFICATE OF CORRECTION (continued)

U.S. Pat. No. 8,367,117 B2

IN THE SPECIFICATION:

Column 3, lines 12-14:

Now reads: "5-30 percent by weight HA, 5-30 percent by weight gelatin and preferably 10-25 percent by weight HA, 10-25 percent by weight gelatin."

Should read: -- 35-60 percent by weight HA, 35-60 percent by weight gelatin and preferably 45-55 percent by weight HA, 45-55 percent by weight gelatin. --

Column 3, lines 15-18:

Now reads: "5-30 percent by weight HA, 5-30 percent by weight gelatin and 40-90 percent by weight nanoclay and preferably 10-25 percent by weight HA, 10-25 percent by weight gelatin and 50-80 percent by weight nanoclay."

Should read: -- 35-60 percent by weight HA, 35-60 percent by weight gelatin and 1-20 percent by weight nanoclay and preferably 45-55 percent by weight HA, 45-55 percent by weight gelatin and 1-10 percent by weight nanoclay. --

Column 3, lines 54-56:

Now reads: "about 1:3 to about 1:25, more preferably from about 1:5 to about 1:20 and most preferably from about 1:10 to 1:15."

Should read: -- about 6:1 to about 1:2, and most preferably from about 3:1 to 1:1. --

Column 4, lines 43-45:

Now reads: "about 1:5 to about 1:20 and the most preferred volume ratio is from about 1:10 to about 1:15."

Should read: -- about 5:1 to about 1:2 and the most preferred volume ratio is from about 2:1 to about 1:1. --